(12) United States Patent
Konwinski et al.

(10) Patent No.: US 6,887,498 B2
(45) Date of Patent: May 3, 2005

(54) METHOD OF MAKING BOWMAN-BIRK INHIBITOR PRODUCT

(75) Inventors: Arthur H. Konwinski, Fort Wayne, IN (US); Bernard F. Szuhaj, Fort Wayne, IN (US)

(73) Assignee: SOLAE, LLC, St. Louis, MO (US)

( * ) Notice: Subject to any disclaimer, the term of this patent is extended or adjusted under 35 U.S.C. 154(b) by 0 days.

(21) Appl. No.: 10/197,297

(22) Filed: Jul. 16, 2002

(65) Prior Publication Data

US 2003/0026861 A1 Feb. 6, 2003

Related U.S. Application Data

(60) Provisional application No. 60/306,688, filed on Jul. 20, 2001.

(51) Int. Cl.$^7$ ................................................ A61K 35/78
(52) U.S. Cl. ........................ 424/757; 424/776; 435/213
(58) Field of Search ............................. 424/757, 776; 435/213

(56) References Cited

U.S. PATENT DOCUMENTS

| | | | |
|---|---|---|---|
| 4,793,996 A | | 12/1988 | Kennedy et al. |
| 5,217,717 A | | 6/1993 | Kennedy et al. |
| 5,338,547 A | * | 8/1994 | Kennedy et al. |

OTHER PUBLICATIONS

Skoog et al. (Fundamental of Organic Chemistry (1988): Saunders College Publishing, New York, p. 736).*
Baturay et al., "Pyrene Acts as a Cocarcinogen with the Carcinogens Benzo [A] Pyrene, β–Propiolactone and Radiation in the Induction of Malignant Transformation in Cultured Mouse Fibroblasts; Soybean Extract Containing the Bowman–Birk Inhibitor Acts as an Anticarcinogen", 1986 *Cell Biology and Toxicology* 2:21–32.
Birk et al., "Isolation of Tribolium–proteolytic–enzyme–inhibitor from soybeans", 1962 *Bull. Res. Council Israel* Sec. A 11:48.
Birk et al., "Separation of a Tribolium–protease inhibitor from soybeans on a calcium phosphate column", 1963 *Biochim. Biophys. Acta*, 67:326–328.

Hwang et al., "Purification, Partial Characterization, and Immunological Relationships of Multiple Low Molecular Weight Protease Inhibitors of Soybean", 1977 *Biochim. Biophys. Acta* 495:369–382.
Kakade et al., "Determination of Trypsin Inhibitor Activity of Soy Products:A Collaborative Analysis of an Improved Procedure", 1974 Cereal Chemistry, 51: 376–382.
Kassell B., Trypsin and Chymotrypsin Inhibitors from Soybeans, 1970 *Methods in Enzymology* 19: 860–861.
Kennedy et al., "Anticarcinogenic Actions of Protease Inhibitors", in *Anticarcinogenesis and Radiation Protection*, edited by Cerutti et al., Plenum Pub. Co., 1987 pp. 285–295.
Messadi et al., "Inhibition of Oral Carcinogenesis by a Protease Inhibitor", 1986 *JNCI* 76:447–452.
Morris A., "Factors Influencing Experimental Carcinogenesis in the Hamster Cheek Pouch", *J. Dent. Res.* 1961 40:3–15.
Salley J., "Experimental Carcinogenesis in the Cheek Pouch of the Syrian Hamster", 1954 *J. Dent. Res.*, 33:253–262.
St. Clair et al., "Suppression of dimethylhydrazine–induced carcinogenesis in mice by dietary addition of the Bowman–Birk Protease Inhibitor", 1990 *Cancer Res.* 50:580–586.
Weed et al., . "Protection against dimethylhydrazine–induced adenomatous tumors of the mouse colon by the dietary addition of an extract of soybeans containing Bowman–Birk protease inhibitor", 1985 *Carcinogenesis* 6:1239–1241.
Yavelow et al., "Nanomolar concentrations of Bowman--Birk soybean protease inhibitor suppress x–ray–induced transformation in vitro", 1985 *Proc. Natl. Acad. Sci.* USA 82:5395–5399.
Yavelow et al., "Bowman–Birk Soybean Protease Inhibitor as an Anticarcinogen", 1983 *Cancer Res.* 43:2454–2459.

* cited by examiner

*Primary Examiner*—Susan D. Coe
(74) *Attorney, Agent, or Firm*—James L. Cordek; Cary A. Levitt

(57) ABSTRACT

A method for preparing a Bowman-Birk inhibitor (BBI) product from soybeans is provided. The product produced in accordance with the method of the invention and compositions including the product are also provided. BBI product produced in accordance with the invention is a significantly improved inhibiter of malignant cell transformation and methods for its administration to prevent or inhibit progression of cancer are provided.

15 Claims, No Drawings

METHOD OF MAKING BOWMAN-BIRK INHIBITOR PRODUCT

This application claims the benefit of U.S. Provisional Application No. 60/306,688,filed Jul. 20, 2001.

BACKGROUND OF THE INVENTION

This invention relates to a new method of producing an acetone extracted Bowman-Birk Inhibitor (BBI) product from the soybean and the product produced thereby and compositions comprising this product.

BBI products have been shown to exhibit inhibitory activity against the malignant transformation of cells under certain conditions and its administration to affect various forms of cancer. It has been shown that the enzyme-inhibitor described by Bowman (*Proc. Soc. Exptl. Med.*, 63:547 (1946)) and Birk et al. (*Bull. Res. Council Israel*,Sec. A 11:48 (1962) and *Biochim. Biophys. Acta*, 67:326 (1963)), and subsequently referred to as the Bowman-Birk Inhibitor (BBI), possesses certain physiological activity that prevents, or at least greatly reduces, radiologically or chemically induced malignant transformation of cells in culture and in experimental animals. Yavelow et al. (*Proc. Natl. Acad. Sci.*, USA 82:5395–5399 (1985)) reported that a crude soybean extract, if defatted with acetone, effectively blocked cell transformation in vitro. An active component of this crude extract is the BBI. These observations, with epidemiological data, suggested BBI as a putative dietary anticarcinogen, particularly with respect to colon cancer.

Weed et al. (*Carcinogenesis*, 6:1239–1241 (1985)) disclose that an extract of soybeans containing the Bowman-Birk protease inhibitor added to the diet of dimethylhydrazine (DMH)-treated mice resulted in a significant suppression of odenomatous tumors of the colonic mucosa. DMH-induced colon cancer in mice is generally regarded as an excellent animal model for the human disease, with carcinogen treatment inducing adenocarcinomas of the colon and rectum which are similar to the tumors arising in the human colon suggesting the possibility that a dietary additive of the sort studied might confer some protection against the development of human colon cancer without undesirable side effects. The BBI extract and methods for its preparation were as described by Yavelow et al. *Cancer Res.*, 43:2454–2459 (1983); *Proc. Natl. Acad. Sci.*,USA 82:5395–5399 (1985) and Hwang et al. *Biochim. Biophys. Acta*, 495:369–382 (1977).

Messadi et al. (*JNCI*, 76:447–452 (1986)) demonstrated that a soybean extract containing the protease inhibitor BBI suppresses 7,12-dimethyl-benz[a]anthracene (DMBA)-induced carcinogenesis in the hamster cheek pouch. This oral cancer model, with the use of the hamster check pouch carcinogenesis system, has the same histopathology, growth pattern, and precancerous lesions as the most common form of human oral cancer, squamous cell carcinoma. It was shown in this study that hamster cheek pouch carcinogenesis can be inhibited by BBI and suggested that human oral carcinogenesis might respond to BBI in a comparable manner. The BBI preparation used in this study was a crude extract of the inhibitor prepared as described by Yavelow et al. (*Proc. Natl. Acad. Sci.*,USA 82:5395–5399 (1985)).

Baturay et al. (*Cell Biology and Toxicology*, 2:21–32 (1986)) disclose that a BBI preparation, wherein a crude soybean extract is defatted with acetone, suppresses radiation and chemically induced transformation in vitro, with or without enhancement by the co-carcinogen, pyrene. Yavelow et al., 1985,show that either pure BBI or the BBI extract prepared in accordance with their methods suppresses radiation induced transformation in C3H10T½ cells. Kennedy et al, 1984, report that either pure BBI or the BBI extract prepared in accordance with their method reduce the levels of chromosome abnormalities in cells of patients with Bloom's syndrome (a genetic disease in which the high levels of chromosome abnormalities are thought to predispose the patients to a higher than normal cancer incidence). Still, other studies suggest that soybean-derived protease inhibitors can have suppressive effects on skin, breast and liver carcinogenesis in vivo.

Kennedy et al. in *Anticarcinogenesis and Radiation Protection*,edited by Cerutti et al., Plenum Pub. Co., pp. 285–295 (1987), disclose that BBI suppresses carcinogenesis in various systems using a crude BBI extract prepared by defatting soybeans with acetone. Their results suggested that very low concentrations of BBI-type protease inhibitor preparations would be effective as chemopreventative agents for colon cancer. There was no evidence to suggest that the use of protease inhibitors as chemopreventative agents would be complicated by possible toxicity problems.

St. Clair et al. (*Cancer Res.*, 50:580–586 (1990)) report that the addition of 0.5% or 0.1% semi-purified BBI or 0.1% or 0.01% purified BBI to the diet of DMH-treated mice resulted in a statistically significant suppression of angiosarcomas and nodular hyperplasia of the liver and colon carcinogenesis. The results of this study also indicate that BBI, included as 0.5% of the diet or less had no adverse effect upon the health of the mice but had the capacity to suppress liver and colon carcinogenesis.

Perlmann et al. (*Methods in Enzymology*, 19: 860–861 (1970)) have described an elaborate method for obtaining the BBI from a defatted soybean extract.

U.S. Pat. No. 4,793,996 (Kennedy et al.) discloses a process comprising treating soybeans with acetone, followed by ethanol extraction and acetone precipitation for obtaining BBI. The soybeans may be defatted prior to acetone treatment. In addition, BBI may be further purified by conventional techniques. Kennedy et al. discovered that in the conventional process for preparing BBI from soybeans, a factor remained which adversely affected the ability of BBI to inhibit the malignant transformation of cells. If the factor was removed, the resulting BBI product was capable of inhibiting the malignant transformation of cells. It was found to be possible to remove this factor by treating the soybeans with acetone prior to the ethanol extraction step taught by Perlmann et al.

Kennedy et al. teach that it is unnecessary to carry out a procedure requiring complete purification of the extract to the point where the product contains only a single protein, but instead it has been found effective to stop the purification procedure at a point where a crude inhibitor extract is obtained. This crude extract (i.e., concentrate) is itself edible and can be used as an inhibitor of malignant transformation of cells, for example by oral ingestion. Kennedy et al. disclose a process for preparing a crude soybean extract containing an inhibitor of malignant cell transformation which comprises defatting soybeans and extracting said inhibitor from said defatted soybeans; the improvement comprises defatting said soybeans by bringing them into contact with at least an equal weight of acetone and, thus, producing a crude inhibitor extract having greatly increased effectiveness.

The prior art has also described concentration of BBI from soybean solubles by centrifugation and ultrafiltration, and further purification by acetone precipitation. The separation of soybean solids from hexane-extracted soy flour/flakes in a commercial soy protein concentrates process is well known. Producing a BBI concentrate by these steps alone, i.e., without the use of an aqueous alcohol extraction, is disclosed in U.S. Pat. No. 5,217,717. This patent also teaches that the less solvent used, the more economical and safer the process. Producing waste-solvent streams containing a mixture of alcohol-water-acetone requires very complex and expensive distillation equipment, which is eliminated in the method disclosed in this patent. It is also taught that ultrafiltration is much more efficient than dialysis; one single step of ultrafiltration can remove more solids than 3 days of dialysis. After purification, most of the examples of the present invention employ spray-drying, which is much faster and hence, more economical than lyophilization. It is also disclosed that spray-drying has no effect on BBI recovery, as measured by chymotrypsin inhibition (CI), used as an indicator for the presence of BBI. This patent also teaches that ultrafiltration step(s) can be avoided altogether when the starting material is soy solubles and the acetone treatment is applied to a substrate that has a substantially higher concentration of BBI than that in the defatted soy flour/flake of the prior art, for example, Kennedy et al.

The present invention provides a new method for making a Bowman-Birk product. An acetone extracted Bowman-Birk product having at least 30% soy protein by weight of dry matter and a chymotrypsin inhibitor level of at least 90 milligrams/gram is provided.

SUMMARY OF THE INVENTION

It is an object of the present invention to provide a method for making a Bowman-Birk product comprising providing acid extracted solubles from defatted soybeans; adding acetone to said solubles to form a precipitate; separating liquid from said precipitate; and drying said precipitate. The product made thereby is also an object of this invention.

It is a further object of this invention to provide a method of making a Bowman-Birk inhibitor concentrate without alcohol extraction comprising providing defatted soybean flakes; slurrying said flakes with water; adjusting the pH of said slurry to about 4 to 6.5; mixing said pH adjusted slurry; separating soluble material from said pH adjusted slurry; mixing acetone with said solubles to form a precipitate, with the amount of acetone being about twice as much as the amount of said solubles by weight; decanting liquid from said precipitate; mixing acetone with said precipitate, with the amount of acetone being about half as much as the amount used in the first said acetone mixture; decanting liquid from said second acetone mixture; and vacuum filtering said precipitate.

An acetone extracted Bowman-Birk product having at least 30% soy protein by weight of dry matter and a chymostrypsin inhibitor level of at least 90 milligrams/gram is also an object of the invention.

It is another object of the invention to provide pharmaceutical compositions and dietary supplements comprising a product of the invention.

DETAILED DESCRIPTION OF THE INVENTION

In the process of the present invention, an effective BBI product is produced with a high level of biological activity as measured by CI content and/or the inhibition of radiologically or chemically induced malignant transformation of cells. The method of the invention utilizes acid extracted soybean solubles as a source material that can be recovered directly from a commercial acid-leached soy protein concentrate process. In one embodiment, the soybeans are flaked and defatted with hexane. In one embodiment, the acid extraction is performed at a pH of about 4.5 to 5.5 with hydrochloric acid. In one embodiment, said acid extraction is performed at a pH of about 4.5 and said product has about 30–40% protein by weight of dry matter and a chymotrypsin inhibitor level greater than 140 milligrams/gram. In another embodiment, said acid extraction is performed at a pH of about 5.4 and said product has greater than 60% protein by weight of dry matter and a chymotrypsin inhibitor level greater than 100 milligrams/gram. Said acid extraction may be performed with mixing for about one hour. Acetone is added to the soybean solubles to form a precipitate. In one embodiment, the amount of acetone added is about two times the amount of the solubles by weight. The liquid is separated from the precipitate and the precipitate is dried. The method may further comprise the steps of adding acetone to said precipitate and then separating a second liquid. In this embodiment, the amount of acetone added is about half as much acetone as was added in the first acetone addition step. The method may also include the steps of mixing the acetone with the extracted solubles, allowing the mixture to settle and then mixing the acetone with the precipitate and allowing the second mixture to settle. In this embodiment, the mixing steps are about ten minutes each and the settling steps are for at least one hour each. The precipitate may be vacuum filtered. The drying step may be performed by air drying the filtered precipitate. In one embodiment, the method further comprises the steps of dispersing the dried precipitate in water, filtering said dispersion and then spray drying the dispersion.

A pharmaceutical composition or dietary supplement comprising a product made in accordance with the methods of the invention is provided.

An acetone extracted Bowman-Birk product having at least 30% soy protein by weight of dry matter and a chymotrypsin inhibitor level of at least 90 milligrams/gram is also an object of this invention.

A method of making a Bowman-Birk inhibitor concentrate without alcohol extraction is also provided. In this method, defatted soybean flakes are slurried with water. The pH of the slurry is adjusted to about 4 to 6.5 and the pH-adjusted slurry mixed. Soluble material is then separated from the slurry. Acetone is mixed with the solubles to form a precipitate, with the amount of acetone being about twice as much as the amount of the solubles by weight. The liquid is decanted from the precipitate. Acetone is then mixed with said precipitate, with the amount of acetone being half as much as the amount of acetone used in the first mixing step. Liquid is decanted from said second acetone mixture and the precipitate is vacuum filtered. This method may further comprise air drying said vacuum filtered precipitate, dispersing said air dried precipitate in water, filtering said dispersion and then spray drying the filtered dispersion. In a preferred embodiment, the soybean flakes are defatted with hexane and the pH is adjusted with hydrochloric acid. In one embodiment, the first mixing step is performed for about an hour and the subsequent mixing steps are for about ten minutes each. In one embodiment, the acetone mixtures are allowed to settle for about one hour each before the decanting steps are performed. Pharmaceutical compositions and dietary supplements produced in accordance with these methods are provided.

A Bowman-Birk product having at least 30% soy protein by weight of dry matter and a chymotrypsin inhibitor level of at least 90 milligrams/gram is also provided.

A BBI product produced in accordance with the method of the invention is an effective inhibitor of malignant cell transformation. Methods for the administration of said BBI product to inhibit the malignant transformation of cells and to prevent or inhibit the progression of cancer are well known in the art.

A BBI product produced in accordance with the method of the present invention is highly effective at suppressing DMBA-induced oral carcinogenesis in hamsters at a concentration of 1.0%.

Compositions made in accordance with the various embodiments of the inventions are useful for inhibiting the malignant transformation of cells by administering a BBI product produced in accordance with the teachings of the invention. Said compositions are useful for preventing cancer or inhibiting cancer progression in an animal, such as man, by administering said compositions, either alone or in combination with a pharmaceutically acceptable carrier. Oral administration, either as a prophylactic dietary supplement or a pharmaceutical are contemplated by the teachings of the invention.

The following examples illustrate the practice of this invention, and the characterization and utility of products resulting therefrom.

EXAMPLE 1

220 lb of defatted soybean flakes (white flakes) were mixed with 156 gallons of water. The pH was adjusted to 5.4 using food grade hydrochloric acid. After mixing for one hour, the slurry was centrifuged using a Sharples P660 continuous decanter centrifuge. The centrifuge feed rate was 2 gpm, and the differential backdrive speed was 20 rpm. A total of 929 lb of centrate was collected in a tank, and 1857 lb of acetone was added with mixing. After 10 minutes mixing time, the mixing was stopped and the insoluble material was allowed to settle. After 1 hour, the liquid layer was decanted, and 929 lb of acetone was added with mixing. Again, after 10 minutes mixing time, the mixing was stopped and the insoluble material was allowed to settle. After 1 hour, the liquid layer was decanted, and approximately 660 lb of the material remained in the tank. This material was then vacuum filtered to remove acetone and acetone-soluble material, then air dried. After air drying, the material was dispersed in water, filtered to remove insoluble material, and then spray dried, resulting in 40.7 lb of product. The product contained 5.15% moisture, 64.94% protein, 9.29% ash, and the CI was 103 mg/g. The TI was 47 mg/g.

EXAMPLE 2

220 lb of defatted soybean flakes (white flakes) were mixed with 156 gallons of water. The pH was adjusted to 4.5 using food grade hydrochloric acid. After mixing for one hour, the slurry was centrifuged using a Sharples P660 continuous decanter centrifuge. The centrifuge feed rate was 2 gpm, and the differential backdrive speed was 37 rpm. A total of 804 lb of centrate was collected in a tank, and 1609 lb of acetone was added with mixing. After 10 minutes mixing time, the mixing was stopped and the insoluble material was allowed to settle. After 1 hour, the liquid layer was decanted, and 805 lb of acetone was added with mixing. Again, after 10 minutes mixing time, the mixing was stopped and the insoluble material was allowed to settle. After 1 hour, the liquid layer was decanted, and approximately 558 lb of the material remained in the tank. This material was then vacuum filtered to remove acetone and acetone-soluble material, then air dried. After air drying, the material was dispersed in water, filtered to remove insoluble material, and then spray dried, resulting in 10.45 lb of product. The product contained 6.31% moisture, 37.83% protein, 13.93% ash, and the CI was 146 mg/g. The TI was 79 mg/g.

EXAMPLE 3

As the C3H10T½ cell transformation assay system was the in vitro system in which BBI was first identified as an anticarcinogenic agent, the C3H10T½ cell transformation assay is used for in vitro transformation studies to evaluate the anticarcinogenic activity of a composition made in accordance with the teachings of the present invention. C3H10T½ cells are a mouse embryo fibroblast cell line which can be transformed in culture by chemicals and radiation. When transformed, the cells pile up, forming densely staining foci against a background monolayer of contact-inhibited cells. The transformed foci are characterized as type II or type III using defined morphological criteria. A very high percentage of type II and III foci are tumorigenic when inoculated into syngeneic or nude mice.

To assay for the inhibition of oncogenic transformation by extracts of soybeans, in the in vitro assay, the following protocol is employed: C3H10T½ cells are seeded, and after 24 hours, treated with 600 R of radiation. Immediately after carcinogen treatment, the medium is changed to complete medium containing the sample of interest (at the highest non-toxic level, to at most 1 mM; it has been observed in previous studies that if compounds do not have an effect at this concentration (1 mM) in the medium they will not have an effect at higher levels). Subsequently, the medium is changed at weekly intervals and at 6 weeks. The dishes are fixed and stained and the transformed foci evaluated.

If a new preparation looks promising after being tested for the ability to inhibit transformation in vitro, it is tested for the ability to inhibit carcinogenesis in vitro, specifically 7,12-dimethylbenz(a)anthracene induced oral carcinogenesis in hamsters. The protocol to be utilized for these studies is the same as that described by Messadi et al., 1986.

EXAMPLE 4

Non-inbred male Syrian hamsters, 4 weeks old and weighing 70–90 g. can be obtained from Charles River Breeding Laboratories, Wilmington, Mass. The animals are housed 4 per cage with wood chips for bedding. The environment is controlled with an alternating 12-hour light-dark cycle. Water and Purina Laboratory Chow (45001; Ralston Purina Co., St. Louis, Mo.) are available ad libitum. The hamsters are divided into treatment and control groups.

All treatments are applied topically to the right cheek pouch as described (Salley, *J. Dent. Res.*, 33:253–262 (1954); Morris, *J. Dent. Res.*, 40:3–15 (1961)). Animals are weighed at weekly intervals. DMBA (Sigma Chemical Co., St. Louis, Mo.) is applied in a 0.25% solution in heavy mineral oil (U.S.P.) at a dose of 0.125 mg on the cheek pouch 3 times per week for 8 weeks of treatment (i.e., 0.375 mg/wk); this is a standard protocol for DMBA-induced hamster cheek pouch carcinogenesis (Salley, (1954); Morris, (1961)).

All animals are treated for 20 weeks and then sacrificed by $CO_2$ inhalation. The time between the last application of DMBA and animal sacrifices is approximately 4 months. At the time of autopsy, all organs are examined and any organs having an abnormal appearance are removed for histopathologic analysis. The location of all tumors is noted and the size in mm is recorded. The cheek pouches are carefully examined, photographed, and then prepared for histopathologic analysis. Each pouch is fixed in 10% buffered formalin and embedded in paraffin. Five-micron sections are cut and stained with hematoxylin and eosin.

For each animal of each treatment group, the results of the cheek pouch histopathologic analysis are determined. Histopathological alterations observed in organs other than the cheek pouch are also noted.

The conclusions that can be drawn from the data in such studies are as follows. When present for the entire carcinogenesis assay period (0–180 days), BBI significantly suppresses DMBA induced oral carcinogenesis at concentrations from 1% down to 0.01%. 1% BBI applications at 5 times per week, 3 times per week and once per week (for the entire carcinogenesis assay period; 0–180 days), lead to a significant reduction in the DMBA induced tumor yield.

EXAMPLE 5

The method used for chymotrypsin inhibitor (CI) analysis is based on the American Oil Chemists' Society (AOCS) official method Ba-12-75 for trypsin inhibitor activity for soy products, differing in the enzyme and substrate used. The substrate used for CI analysis is N-Glutaryl-L-Phenylalanine-p-nitroanilide (GPNA), available from Sigma Chemicals as G2505.The enzyme used is L-Chymotrypsin, Type II—Bovine pancreatic alpha chymotrypsin, available from Sigma Chemicals as C4129. The AOCS method is based upon Kakade et al. (Cereal Chemistry, 51. 376 (1974)).

Chymotrypsin hydrolyzes the substrate glutaryl-L-phenylalanine-p-nitroanilide present in excess. The release of p-nitroanilide, a yellow dye, is measured spectrophotometrically. In the presence of soy protein product, the release of p-nitroanilide changes inversely with the level of active chymotrypsin inhibitor.

What is claimed is:

1. A method for making a Bowman-Birk product comprising:
    introducing and mixing acetone with acid extracted solubles from defatted soybeans wherein the amount of acetone is about two times (by weight) the amount of acid extracted solubles;
    allowing the acetone and acid extracted solubles mixture to settle for at least 1 hour to form a precipitate;
    separating the precipitate from the liquid by decantation;
    introducing and mixing acetone with the separated precipitate wherein the amount of acetone is about one half of the amount by weight utilized in the first mixing step;
    allowing the acetone and separated precipitate mixture to settle;
    separating the precipitate from the liquid by decantation;
    vacuum filtering the separated precipitate and drying the precipitate by air drying;
    dispersing the air dried precipitate in water;
    filtering the dispersion to remove insoluble materials; and spray drying the dispersion.

2. The method of claim 1 wherein said soybeans are flaked and defatted with hexane.

3. The method of claim 1 wherein said acid extracted solubles are obtained by acid extraction performed at a pH of about 4.5–6.5 with hydrochloric acid.

4. The method of claim 3 wherein said acid extraction is performed with mixing for about 1 hour.

5. The method of claim 1 wherein said mixing steps are for about 10 minutes each.

6. The method of claim 5 wherein said settling steps are for at least 1 hour each.

7. The method of claim 1 wherein said acid extracted solubles are obtained by acid extraction performed at a pH of about 4.5 and said dispersion has about 30–40% protein by weight of dry matter and a chymotrypsin inhibitor level greater than 140 milligrams/gram.

8. The method of claim 1 wherein said acid extracted solubles are obtained by acid extraction performed at a pH of about 5.4 and said dispersion has greater than 60% protein by weight of dry matter and a chymotrypsin inhibitor level greater than 100 milligrams/gram.

9. A pharmaceutical composition or dietary supplement comprising the product made in accordance with the method of claim 1.

10. A method for making a Bowman-Birk inhibitor concentrate without alcohol extraction comprising:
    slurrying defatted soybean flakes with water;
    adjusting the pH of said slurry to about 4–6;
    mixing said pH adjusted slurry;
    separating soluble material from said pH adjusted slurry;
    mixing acetone with the soluble material and allowing the mixture to settle for at least 1 hour to form a precipitate, wherein the amount of acetone is about two times (by weight) the amount of the soluble material;
    separating the precipitate from the liquid by decantation;
    mixing acetone with said precipitate, wherein the amount of acetone is about one half the amount by weight utilized in the first mixing step
    separating the precipitate from the liquid by decantation;
    vacuum filtering the separated precipitate and drying the precipitate by air drying;
    dispersing the air dried precipitate in water;
    filtering the dispersion to remove insoluble materials; and spray drying the dispersion.

11. The method of claim 10 wherein said soybean flakes are defatted with hexane and the pH is adjusted with hydrochloric acid.

12. The method of claim 10 wherein said slurry mixing step is performed for about 1 hour and said acetone mixing steps are performed for about 10 minutes each.

13. The method of claim 12 further comprising allowing said acetone mixtures to settle for about 1 hour each before said decanting steps.

14. The method of claim 10 wherein said pH is about 5 and the amount of said dispersion is about 10% of the amount of said flakes by weight, with said dispersion having a chymotrypsin inhibitor level of about 120 milligrams/gram.

15. A pharmaceutical composition or dietary supplement comprising a product made in accordance with the method of claim 10.

* * * * *